(12) United States Patent
Merkel et al.

(10) Patent No.: US 9,447,021 B2
(45) Date of Patent: *Sep. 20, 2016

(54) PROCESS FOR THE PURIFICATION OF ANILINE FROM GAS PHASE HYDROGENATIONS

(71) Applicant: Bayer Intellectual Property GmbH, Monheim (DE)

(72) Inventors: Michael Merkel, Dusseldorf (DE); Peter Lehner, Baytown, TX (US); Bastian Mahr, Cologne (DE); Amgad Salah Moussa, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/385,822

(22) PCT Filed: Mar. 18, 2013

(86) PCT No.: PCT/EP2013/055566
§ 371 (c)(1),
(2) Date: Sep. 17, 2014

(87) PCT Pub. No.: WO2013/139737
PCT Pub. Date: Sep. 26, 2013

(65) Prior Publication Data
US 2015/0080610 A1    Mar. 19, 2015

(30) Foreign Application Priority Data
Mar. 23, 2012 (EP) .................................... 12160920

(51) Int. Cl.
*C07C 209/84* (2006.01)
*C07C 209/36* (2006.01)

(52) U.S. Cl.
CPC .......... *C07C 209/84* (2013.01); *C07C 209/36* (2013.01)

(58) Field of Classification Search
CPC ......................... C07C 209/84; C07C 209/36
See application file for complete search history.

(56) References Cited

U.S. PATENT DOCUMENTS

| 5,808,157 | A | 9/1998 | Langer et al. |
| 5,877,350 | A | 3/1999 | Langer et al. |
| 7,692,042 | B2 | 4/2010 | Dugal et al. |
| 8,455,691 | B2 | 6/2013 | Sommer et al. |
| 2007/0238901 | A1 | 10/2007 | Dugal et al. |
| 2008/0234518 | A1 | 9/2008 | Sommer et al. |

FOREIGN PATENT DOCUMENTS

| DE | WO2012052407 | * | 4/2012 | .......... C07C 209/84 |
| EP | 1670747 B1 | | 5/2009 | |
| JP | 49035341 A | | 4/1974 | |
| JP | 08295654 A | | 11/1996 | |
| JP | 2005350388 A | | 12/2005 | |
| JP | 2007217405 A | | 8/2007 | |

* cited by examiner

Primary Examiner — Clinton Brooks
(74) Attorney, Agent, or Firm — N. Denise Brown

(57) ABSTRACT

The present invention relates to a process for the purification of aniline which originates from gas phase hydrogenations. In this process, only a minimum proportion of the aniline has to be evaporated and condensed again. The process is highly efficient in removing compounds which have phenolic hydroxyl groups and results in minimal losses of aniline. This process also reduces the unwanted coupling mechanisms in the division of the overall crude product in the fraction condensation into individual substreams and the subsequent workup of these.

12 Claims, 4 Drawing Sheets

PROCESS FOR THE PURIFICATION OF ANILINE FROM GAS PHASE HYDROGENATIONS

CROSS REFERENCE TO RELATED APPLICATIONS

This is the U.S. national stage of International application PCT/EP2013/055,556, filed Mar. 18, 2013 designating the United States and claiming priority to European application 12160920.0 filed Mar. 23, 2012.

FIELD OF THE INVENTION

The invention relates to a process for purifying aniline obtained by gas phase hydrogenation of nitrobenzene, by fractional condensation of the crude reaction product obtained in gaseous form in n condensation stages with successively falling condensation temperature, distillation of some or all of the condensates obtained in condensation stages 1 to (n−1) (the partial condensates PK$^i$) to obtain a distilled product PKD, combination of the distilled condensates PKD with at least, preferably exclusively, the organic fraction of the nth condensate (the total condensate TK) and, if present, with at least some of the undistilled partial condensates PK$^i$ remaining, and extraction of the product mixture thus obtained with aqueous base solution.

BACKGROUND

Aromatic amines are important intermediates which have to be available inexpensively and in large volumes. Aniline, an aromatic amine of particular industrial significance, can be purified in an outstanding manner by the process according to the invention. Aniline is an important intermediate in the preparation of di- and polyisocyanates of the diphenylmethane series (MDI) and is prepared on the industrial scale generally by catalytic hydrogenation of nitrobenzene. For this purpose, it is necessary to build plants having very large capacities in order to be able to cover the enormous global demand. Preferably, the hydrogenation of nitrobenzene is conducted in the gas phase over fixed, heterogeneous supported catalysts, for example Pd on alumina or carbon supports, in fixed bed reactors at an absolute pressure of 2-50 bar and a temperature in the range of 250-500° C. under adiabatic conditions in cycle gas mode; see EP-A-0 696 573, EP-A-0 696 574 and EP-A-1 882 681. "Cycle gas mode" means that the uncondensable gases present in the crude reaction product (i.e. essentially hydrogen unconverted during the hydrogenation and any inert gases which have been added or formed through side reactions), possibly with the exception of small amounts branched off to keep the concentrations of further gaseous components constant in the cycle gas—for instance of ammonia formed as a result of deamination reactions on the catalyst—are recycled into the reaction.

In the preparation of aniline by hydrogenation of nitrobenzene, not only the target product but also water and organic secondary components are formed. In addition, according to the production process and state of operation, fractions of unconverted nitrobenzene may also be present. These organic secondary components and any unconverted nitrobenzene have to be removed down to residual contents of a few ppm before further use of the aniline. The organic secondary components and any unconverted nitrobenzene can be divided into two groups: a) the group of the "low boilers", i.e. compounds or azeotropically boiling mixtures of individual components having boiling points below those of aniline (b.p.=184° C.), and b) the group of the "high boilers", i.e. compounds or azeotropically boiling mixtures of individual components having boiling points above those of aniline. Nitrobenzene (b.p.=211° C.) accordingly forms part of the group of the high boilers. Because of the similarity of its boiling point to aniline, it is possible only with difficulty to remove phenol by a distillative route (see, for example, EP-A-1 670 747), the latter being an ever-present by-product in industrial hydrogenations of nitrobenzene.

A crude product stream of a gas phase hydrogenation of nitrobenzene thus generally consists of
 (1) aniline,
 (2) process water (which is the sum total of water formed in the reaction and any water present in the reactant gas stream),
 (3) (uncondensable gases (uncondensable under customary industrial conditions for aniline workup) (excess hydrogen—optionally containing gaseous impurities, for example methane and any added inert gases, for example nitrogen added to improve selectivity (cf. EP-A-1 882 681), and any gaseous by-products, for example ammonia from deamination reactions),
 (4) low boilers and
 (5) high boilers (which may possibly also contain fractions of unconverted nitrobenzene).
(1), (2), (4) and (5) are also referred to collectively hereinafter as "condensable constituents".

The state of the art is to free the aniline of all secondary components by distillation. Because of the high-boiling fractions in crude aniline (e.g. diphenylamine having b.p.=302° C.), it is necessary for this purpose to vaporize the entirety of the aniline and condense it again at least once in the distillation, according to the reflux ratio, such that the distillation process incurs high energy costs.

A particular difficulty is the removal of those secondary components whose boiling points are very similar to that of aniline, because the distillation complexity here is considerable. In this connection, especially the removal of phenol (b.p.=182° C.) represents a great challenge for the distillation methodology, which is reflected in the use of long distillation columns with a large number of plates and high reflux ratios, with correspondingly high capital costs and energy expenditure. Compounds having phenolic hydroxyl groups, i.e. compounds bearing at least one hydroxyl group (—OH) directly on an aromatic ring, can generally be problematic in the workup of aniline. As well as phenol, which has already been mentioned, these include the various aminophenols. Although these are easier to remove by distillation because of the higher boiling point, they can cause both a viscosity rise in the column bottom and deposits in the distillation apparatus when bases, for example alkali metal hydroxide, are present in the distillation apparatus in order to optimize the phenol removal.

The purification of aniline is therefore not trivial and is of great industrial significance. Many approaches are dedicated particularly to the problems mentioned in connection with compounds having phenolic hydroxyl groups. The approach to a solution involves converting the compounds having phenolic hydroxyl groups, by reaction with suitable bases, to the corresponding salts which can be removed much more easily as nonvolatile compounds.

For instance, JP-A-49-035341, EP-A-1 845 079, EP-A-2 028 176 and EP-A-1 670 747 disclose processes in which an aromatic amine is distilled in the presence of a base. In this procedure, problems resulting from solids deposition, fouling and/or a significant viscosity rise in the course of distillation have to be prevented by complex and/or costly measures.

As an alternative to the removal of compounds having phenolic hydroxyl groups from aniline during the distillation, JP-A-08-295654 describes an extraction with dilute aqueous alkali metal hydroxide solution and subsequent distillation of the organic phase. Disadvantages of this process are the high NaOH consumption and the occurrence—as a result of the low concentration of the alkyl metal hydroxide solutions—of very large amounts of alkali metal phenoxide-containing wastewater, in addition to the high energy consumption in the distillation.

EP-A-1 845 080 describes a process for purifying aniline by extraction with aqueous alkali metal hydroxide solution of concentration >0.7% by mass, wherein concentration and temperature are adjusted such that the aqueous phase is always the lower phase in the subsequent phase separation. Optionally, to attain a desired product quality, the overall crude product can again be distilled before or after the extraction.

JP-A-2007217405 describes a process in which the phenol-containing aniline is contacted at least twice with aqueous alkali metal hydroxide solution in such a way that the concentration of alkali metal hydroxide in the aqueous phase is between 0.1% by mass and 0.7% by mass. This is followed by a separation of aqueous and organic phase and distillation of the organic phase.

The improvement of aniline workup is addressed in quite general terms by JP-A-2005 350388. A process is described in which a portion of the bottom product of the aniline distillation column is removed therefrom and converted separately to the gas phase, i.e. in a second evaporator other than the actual column evaporator. The gas phase thus obtained is recycled into the pure aniline column; unevaporable high boiler components are removed. A disadvantage of this process is that low boilers and water have to be removed upstream of the actual aniline distillation column, in a process which is complex in terms of apparatus, separately in a dewatering column by an additional distillation.

None of these publications mentioned so far addresses how it is possible to achieve reduction in the proportion of the aniline which has to be evaporated and condensed again in a distillation process. If the aniline to be purified originates from a gas phase process, it actually passes through two condensations according to the prior art: first of all, the reaction product obtained in gaseous form is condensed substantially completely, the aqueous phase is removed and the organic phase obtained is distilled, i.e. the desired product is (i) condensed, (ii) evaporated and (iii) condensed again, which is very energy- and apparatus-intensive and leads to thermal stresses on the aniline.

Only in the as yet unpublished application with reference number PCT/EP2011/068122 is this problem addressed. This describes fractional condensation of the aniline from a gas phase process, with introduction of the product stream originating from the partial condensation (PK) into the lower section of the distillation column between the lowermost stripping section and the subsequent section, and introduction of the product stream originating from the total condensation (TK) into the top of the distillation column above the uppermost rectifying section. Distilled aniline is withdrawn from the distillation column in a sidestream between the lowermost stripping section and uppermost rectifying section. This embodiment achieves the effect that the product stream originating from a total condensation need not be evaporated, but is instead freed of low boilers directly in the distillation column by stripping.

Since the removal of phenol by a distillative route is problematic, the process described requires several extractions, namely individual extractions for each product stream (design as per FIG. 3 in PCT/EP2011/068122). If, moreover, the ingress of salts into the distillation apparatus is to be prevented, each of these extractions additionally has to be followed downstream by a further extraction stage in which the product stream is washed with water. Alternatively, the extraction may also follow the distillation (design as per FIG. 4 in PCT/EP2011/068122), but already stripped product in this case has to be saturated again with water and may need to be subjected to another stripping. Another disadvantage is the strong coupling between the individual condensates, which arises through utilization of the product vapor ascending out of PK in the distillation apparatus in order to strip the product stream originating from TK. According to the product quality, this leads to increased energy intensity because, for example, in spite of a low content of low boilers in the product stream from PK, a high proportion of the overall product has to be run as PK into the lower section of the column and evaporated, in order to assure sufficient stripping of the product stream from TK. In other words, the separation of the overall crude product into TK and PK cannot always be effected as would be desirable for the purposes of an economically optimal workup; instead, it is always also subject to certain constraints which arise from the type of distillation. There are thus unsatisfactory coupling mechanisms in the case of division of the overall crude product in the fractional condensation into individual substreams and the subsequent workup thereof.

There is therefore a need for a process for purifying aniline originating from gas phase hydrogenations, in which only a minimum proportion of the aniline itself has to be evaporated and condensed again, and in which the removal of compounds having phenolic hydroxyl groups is achieved with maximum efficiency with minimum losses of valuable aniline. More particularly, unwanted coupling mechanisms in the division of the overall crude product in the fractional condensation into individual substreams and the subsequent workup thereof should also be reduced to a minimum.

SUMMARY

Taking account of the above, the present invention provides a process for preparing aniline, comprising the following steps:
(i) gas phase hydrogenation of nitrobenzene in the presence of a catalyst,
(ii) fractional condensation of the gaseous crude product obtained in (i) in n condensation stages, where n is a natural number from 2 to 8, preferably from 3 to 4, and is more preferably 3, with gradually falling condensation temperature, giving a liquid partial condensate $PK^i$ ($PK^1$, $PK^2$, ... $PK^{n-1}$) in each of the first to (n−1)th condensation stages and a liquid total condensate (TK) in the nth condensation stage,
(iii) if (a) n=2, distillation of the one liquid partial condensate $PK^1$ obtained in (ii),
    if (b) n≥3, distillation of some of the liquid partial condensates $PK^i$ obtained in (ii), preferably only of the first partial condensate $PK^1$,
    to obtain a distillate PKD, preferably only $PK^1D$ (i.e. the distillate from $PK^1$), (iv) combination of
   (a) if present, at least some of, preferably all, the partial condensates $PK^i$ obtained in (ii) and not distilled in (iii),
   (b) the distillate PKD obtained in (iii) and
   (c) at least, preferably exclusively, the organic fraction of the total condensate TK,
   extraction of the product mixture thus obtained with aqueous base solution and separation of the mixture thus obtained into an aqueous phase and an organic, aniline-comprising phase.

Figure 1:
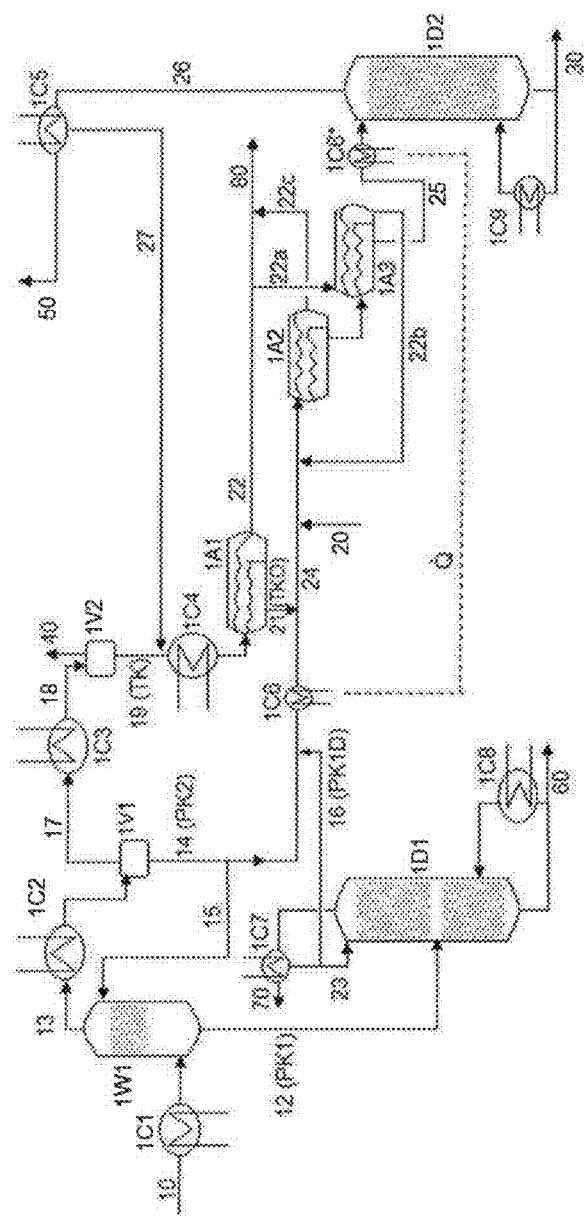
FIG. 1 is a side elevation view of a gas phase hydrogenation process for purification of aniline in accordance with one embodiment of the invention as described herein.

The invention is elucidated in detail hereinafter. Various embodiments can be freely combined here with one another, unless the opposite is clearly apparent to the person skilled in the art from the context.

The gas phase hydrogenation of nitrobenzene in step (i) is effected continuously, and can be effected by any process known from the prior art and over all catalysts known from the prior art. Both isothermal and adiabatic processes have been described. Particular preference is given to the processes described in EP-A-0 696 573, EP-A-0 696 574 and EP-A-1 882 681 (adiabatic process regime) and those described in GB-A-1452466 and EP-A-0 944 578 (isothermal process regime). The adiabatic processes are particularly preferred; among these, the process described in EP-A-1 882 681 is the most preferred. As well as the processes mentioned with stationary catalyst beds, those having fluidized catalyst beds have also been described, for example in DE-1114820-B, DE-1133394-B or WO-2008-034 770 A1. These too can be employed in step (a) of the invention. Preference is given, however, to stationary catalyst beds. Particular preference is given to the catalysts described in EP-A-1 882 681 (paragraphs [0035] to [0050]).

A feature common to all processes is that the crude product is obtained in gaseous form.

This gaseous crude product obtained in step (i) is then fractionally condensed in step (ii), meaning that the crude product from (i) is first cooled in a first condensation stage to such an extent that only a portion of the condensable constituents is liquefied (namely, as well as aniline, predominantly those having the highest boiling point, i.e. compounds from the group of the high boilers). Thus, in the first condensation stage, only a partial condensate ($PK^1$) is obtained. The gas phase of the first condensation stage is fed to the second condensation stage, etc. Only in the last (nth) condensation stage is the incoming gas phase cooled to such an extent that the condensable constituents condense substantially completely (total condensation, TK). Since there are limits to the cooling because of economic boundary conditions, it is not possible to rule out small amounts of condensable constituents remaining in the gas phase. Preferably, the process water is predominantly liquefied only in the total condensation stage (the nth condensation stage), such that all the partial condensates obtained beforehand are preferably monophasic. Between the first and nth condensation stage, there are 0 to 6, preferably 1 to 2, further partial condensation stages $PK^2$, $PK^3$ etc. More preferably, step (ii) of the process according to the invention comprises exactly three condensation stages with three condensate streams, $PK^1$, $PK^2$ and TK.

Useful apparatus for the performance of the fractional condensation in principle includes all apparatus known to those skilled in the art for the purpose of condensation of gases. Examples include air coolers or heat exchangers, for example shell and tube heat exchangers or plate heat exchangers, where the heat released can be utilized for heating of another gaseous or liquid stream.

Preferably, the first condensation stage is operated at a temperature $T^1$ of 100° C. to 200° C., more preferably of 100° C. to 150° C., the nth condensation stage at a temperature $T^n$ of 15° C. to 90° C., preferably of 20° C. to 80° C., more preferably of 40° C. to 70° C., and the temperature of every further condensation stage, if present, is preferably in each case 1 K to 100 K, more preferably in each case 2 K to 50 K, most preferably 5 K to 40 K, below the upstream condensation stage, although the temperature stages need not be equally distributed. In the case of more than three condensation stages, the first and last temperature steps are preferably greater than those in between.

It may also be advantageous, in the course of a reaction cycle of the gas phase hydrogenation, to vary the condensation temperatures, reflux ratio or number of condensation stages utilized, since the selectivity of the hydrogenation is generally poorer at the start of a reaction cycle of the gas phase hydrogenation than at a later time (once all the operating parameters of the gas phase hydrogenation have been adjusted to the optimal conditions and the catalyst has attained its optimal range of action in terms of selectivity) of a reaction cycle. In such a procedure, for example, with falling low boiler content of the crude product stream, the condensation temperature in the first condensation stages would be increased and/or the reflux into the first scrubber would be reduced, in order to reduce the proportion of the aniline to be distilled and hence the energy intensity. If the pressure in the reaction system is varied during the reaction phase (for example increased; cf. EP 6 965 741 B1 paragraphs [0056] to [0057]), it is advantageous also to adjust the condensation temperatures in accordance with physical laws, i.e. to increase them when the pressure is increased and to lower them when the pressure is reduced.

In step (iii), if n≥3, some of the partial condensates $PK^i$ obtained in step (ii), preferably only the first partial condensate $PK^1$, is subjected to a distillation in which a distillate PKD, preferably only $PK^1D$, is obtained, the latter being enriched in aniline compared to the starting partial condensates (i.e., in the preferred embodiment, compared to the first partial condensate $PK^1$). For this purpose, the partial condensates $PK^i$ to be distilled are preferably combined and distilled together. It would also be possible in principle, but in no way preferable because of the great apparatus complexity, to distil each partial condensate individually and to combine the individual distillates $PK^iD$ to give PKD. If n=2, there is only one partial condensate. This is always subjected to a distillation.

Suitable distillation apparatus is all the apparatuses known to those skilled in the art. The distillate PKD is withdrawn either as a sidestream or at the top, preferably at the top of the distillation apparatus.

The last (nth) condensate (TK) contains the majority of the process water and, prior to further processing, is preferably subjected to a phase separation into an aniline-rich organic phase (TKO) and an aqueous phase (TKW). This is done prior to step (iv) in phase separation vessels known to those skilled in the art (e.g. liquid-liquid separators). In this way, it is assured that the phase separation at this point is not disrupted by salts, and a salt-free, water-rich stream is obtained (TKW). In this preferred embodiment, in step (iv), only (c) TKO is combined with (a) if present (in the case that n=2 there are no distilled partial condensates), at least some of, preferably all, the partial condensates $PK^i$ obtained in (ii) and not distilled in (iii) and (b) the distillate PKD obtained in (iii), and the product mixture thus obtained is extracted with aqueous base solution. The mixing of the overall total condensate, i.e. including the process water, with (a) (if present) and (b) is possible in principle, but not preferred, since an additional aqueous stream that would have to be introduced in this case for reduction of the salt burden of the product in a further extraction step would in turn become saturated with product, such that either product losses arise or an additional degree of complexity is necessary for the recovery of the product. Bases used here are preferably aqueous solutions of alkali metal or alkaline earth metal hydroxides (or mixtures of the two). It should be noted here that the concentration of the base solution is selected such that a phase separation reliably takes place, meaning that, firstly, sufficient volumes of both phases (aqueous and organic) are present and, secondly, there is a sufficient density difference at the selected extraction temperature, such that there is no unwanted phase reversal in operation. This can be achieved either by a low or relatively high base concentration (cf. JP-A-08-295654 or EP-A-1 845 080). The mixture obtained in the extraction is separated into an aqueous phase and an organic, aniline-comprising phase. Depending on the exact conditions, the latter may already be sufficiently pure to be sent to the desired use of the aniline. To reduce salt content, however, it may also be appropriate, in an additional, step (v), to scrub the organic, aniline-comprising phase obtained in (iv) with a stream comprising at least 85% by mass of water, based on the total mass of this stream. Preferably, the ratio of the total concentration of salts in this aqueous stream and the aniline-comprising phase is less than 10:1, preferably less than 1:1, more preferably less than 0.1:1. The stream comprising at least 85% by mass of water can be produced, for example, by condensation of water-containing vapors obtained in the production, such that very low salt contents are attained. In the preferred embodiment with a phase separation of TK prior to step (iv), a portion or the entirety of the aqueous phase TKW obtained in the preparation of TKO is more preferably used as a stream comprising at least 85% by mass of water.

Preferably, the aniline-comprising phase—either directly as obtained in (iv) or after scrubbing with said stream comprising at least at least 85% by mass of water—is subjected to a stripping operation. For this purpose, a multitude of embodiments is known to the person skilled in the art. Preference is given to stripping in a distillation apparatus, in which case the aniline-comprising phase is optionally preheated and then applied at the top of the apparatus. At the lower end of the apparatus is a steam-operated circulation evaporator. The aniline depleted of water and low boilers is withdrawn at the base of the apparatus; water and low boilers are removed as vapors overhead. Preferably, aniline entrained out of the vapors is condensed and fed to the total condensate stream.

It is also possible to subject all the water phases that have been contacted with organic phases in the process, i.e., for example, the water phase obtained in (iv) and the aqueous phase (TKW) separated from TK prior to step (iv) in the preferred embodiment, or substreams branched off therefrom, to a steam-heated stripping operation in order to recover aniline as an azeotrope with water, which can then be reused, for example by feeding it to the total condensate stream TK. If such a stripping operation is to be effected, it is found to be particularly advantageous first to combine the aqueous streams to be stripped, and to preheat the wastewater prior to entry into the stripper by heat exchange with aniline vapors from the distillation.

The process is elucidated in detail hereinafter with reference to the appended drawings using the particularly preferred embodiment, which has for its subject-matter the formation of exactly three condensate streams ($PK^1$, $PK^2$ and TK), a separation of TK into an aniline-rich organic phase (TKO) and a water-rich phase (TKW) and a two-stage extraction with subsequent stripping of the scrubbed organic phase. It is a simple matter for the person skilled in the art, on the basis of this description, to modify the process having three condensation stages such that it comprises more than three condensate streams, for instance by introducing additional partial condensation stages $PK^3$, $PK^4$ etc. upstream of the substantially complete last condensation stage (TK).

A preferred embodiment of the process according to the invention is elucidated in detail hereinafter with the aid of FIG. 1.

The labels mean:

TABLE 1

Key for FIG. 1.

| Stream | Definition | Apparatus | Definition |
|---|---|---|---|
| 10 | crude aniline from the hydrogenation | 1A1 | liquid-liquid separator |
| 20 | sodium hydroxide solution | 1A2 | liquid-liquid separator |
| 30 | pure aniline | 1A3 | liquid-liquid separator |
| 40 | excess hydrogen (is returned to the cycle gas, not shown) | 1C1 | cycle gas cooler |
| 50 | offgas | 1C2 | condenser |
| 60 | high boiler purge from the bottom of 1D1 | 1C3 | condenser |
| 70 | offgas from high boiler column | 1C4 | heat exchanger |
| 80 | wastewater | 1C5 | condenser |
| 12 | liquid phase from 1W1, first partial condensate ($PK^1$) | 1C6, 1C6* | heat exchanger |
| 13 | gas stream from 1W1 | 1C7 | condenser |

TABLE 1-continued

Key for FIG. 1.

| Stream | Definition | Apparatus | Definition |
|---|---|---|---|
| 14 | liquid phase from 1V1, second partial condensate (PK$^2$) | 1C8 | evaporator |
| 15 | substream of 14 as reflux into scrubber 1W1 | 1C9 | evaporator |
| 16 | top product from 1D1 (PK$^1$D) | 1D1 | high boiler column |
| 17 | gas stream from 1V1 | 1D2 | aniline stripper |
| 18 | cooled stream from 1C3 | 1V1 | gas-liquid separator |
| 19 | liquid phase from 1V2, total condensate (TK) | 1V2 | gas-liquid separator |
| 21 | organic phase front 1A1, (TKO) | 1W1 | scrubber for retaining high boilers |
| 22 | aqueous phase from 1A1 | | |
| 22a | substream of 22 to 1A3 | | |
| 22b | aqueous phase from 1A3 | | |
| 22c | aqueous phase from 1A2 | | |
| 23 | reflux into the high boiler column | | |
| 24 | combined crude product stream | | |
| 25 | organic phase from 1A3 | | |
| 26 | gas phase from 1D2 | | |
| 27 | condensate from stream 26 | | |
| $\dot{Q}$ | heat integration between 1C6 and 1C6* | | |

The gaseous reaction product, stream 10, consisting of aniline, process water, uncondensable gases, low boilers and high boilers, passes through the three condensation stages under an absolute pressure of 1.0 bar to 50 bar, preferably of 2.0 bar to 20 bar and more preferably of 2.0 bar to 10 bar. The gaseous reaction product is first cooled in heat exchanger 1C1 to 100° C. to 200° C., preferably 100° C. to 150° C., and passed into the scrubber 1W1. At the top of 1W1, stream 13 is withdrawn and cooled in the condenser 1C2 to a temperature of 60° C. to 160° C., preferably of 80° C. to 140° C. and more preferably of 80° C. to 110° C. (condensation leading to formation of PK$^2$). The stream thus obtained is separated in the separator 1V1 into a gaseous phase and liquid phase (PK$^2$). A substream (stream 15) of PK$^2$ can be passed back into the scrubber 1W1, in order to largely retain high boilers from stream 10 and thus to ensure a very substantially high boiler-free stream 13. In this way, a liquid process product rich in high boilers is drawn off from 1W1 (stream 12, PK$^1$). PK$^1$ contains, as well as the high boilers (preferably 90% by mass to 100% by mass of the high boilers present in stream 10), also fractions of aniline (preferably 0.1% by mass to 35% by mass of the aniline present in stream 10), of low boilers (preferably <1% by mass of the low boilers present in stream 10) and of process water (preferably <5% by mass of the process water present in stream 10).

The stream 12 thus obtained is passed into a distillation apparatus 1D1 and distilled therein under reduced pressure, in the course of which the high boilers are in turn enriched in the bottom of the column and separated from the aniline-rich top product (PK$^1$D).

The gaseous stream 17 drawn off from 1V1 is partly condensed in the condenser 1C3, so as to form a liquid process product (condensation leading to formation of TK) in addition to a remaining gas phase. The condensation temperature is guided by the economic boundary conditions: too high a temperature leads to undesirable product losses, too low a temperature to unacceptable energy expenditure for the condensation. The condensation temperature actually selected therefore constitutes a compromise and is preferably from 15° C. to 90° C., more preferably from 20° C. to 80° C. and most preferably from 40° C. to 70° C. In this process step, not only aniline condenses out, but also water and low boilers, and any small proportions of entrained high boilers.

The stream 18 which leaves 1C3 is passed into the separator 1V2, in order to separate the liquid phase from the gaseous phase. The gaseous phase, which comprises the excess hydrogen originating from the reaction, is preferably recycled into the nitroaromatic reduction as cycle gas (stream 40). The liquid process product (TK) drawn off as stream 19 is, optionally after passing through a further heat exchanger, 1C4, separated in a separating vessel (1A1) into an aqueous phase (stream 22) and an organic phase (stream 21, TKO).

The organic product streams 14, 16 and 21 (PK$^2$, PK$^1$D and TKO) are combined and admixed with a base solution, preferably alkali metal hydroxide solution, and optionally with additional water.

Preferably, a relatively highly concentrated base is added first, and the base-containing mixture is mixed thoroughly. The mixing is effected with a mixing unit known to those skilled in the art, preferably by means of a pump. Then the mixture is admixed with further water, preferably a portion of the process water separated from TK, and mixed thoroughly again, preferably by means of a pump, before the aqueous phase is separated from the organic phase in a separating vessel (1A2). In a particularly preferred embodiment of the process according to the invention, the organic phase obtained from 1A2 is subsequently subjected to a second extraction step (1A3). In this case, the process water separated from TK is first used in order to scrub the organic phase from the phenol extraction, and in this way to remove salt residues remaining in the organic phase. After phase separation, the water can then be used for extraction of the base-containing crude product mixture in the first extraction step (1A2) (phenoxide extraction).

At this point, it should be noted that, for reasons of clarity, the liquid-liquid separator in the drawings present here are always drawn in such a way that the organic (aniline-rich) phase settles out at the bottom, while the aqueous (water-rich) phase forms the upper phase. This is of course not always the case in practice. In fact, the particular process parameters, for example temperature and salt content, have an influence on the densities of liquids and can therefore also lead to a reversed arrangement of the phases. This is important for the operability of the invention, but has to be taken into account in the form of a correspondingly altered pipe connection of the separators.

The organic phase from the second extraction stage, as well as aniline, also contains low boilers and water. In order to lower the contents of these secondary components to an on-spec level, the aniline is introduced into a stripping column 1D2 at the top. From the top product stream 26, it is possible to recover a condensate 27 containing aniline and low-boiling secondary components, which is recycled into the phase separation 1A1. Aniline is drawn off in a quality suitable for subsequent processes at the bottom of the stripping column. In order to reduce the energy input in the evaporator 1C9, preheating of the column input 25 can be effected in 1C6*, preferably with exploitation of the heat removed in the cooling in 1C6.

If required, it is possible without any further apparatus complexity to obtain a virtually water-free product (30) by increasing the evaporation rate in 1C9. For the use of the aniline in the preparation of di- and polyamines of the diphenylmethane series (the largest field of use), however, this is not normally required.

The combined process water streams from the extraction stages (stream 80) can, unless used elsewhere in the process, be stripped in a manner known to those skilled in the art (not shown in FIG. 1), in order to clean the process water stream and to recover aniline, for example by recovering an aniline/water mixture as an azeotrope, which is in turn fed into the separating vessel 1A1. In this way, the losses of aniline are minimized.

EXAMPLES

The examples which follow describe the purification of a crude aniline which flows out of a production plant (gas phase hydrogenation) at a mass flow rate of 35 000 kg/h and a temperature of 147° C. and has the following composition.

TABLE 2

Composition of the crude aniline stream to be purified

| Component | Proportion by mass in % |
|---|---|
| Uncondensable gases | 25.50 |
| Low boilers | 0.72 |
| Water | 28.20 |
| Aniline | 45.51 |
| Phenol | 0.02 |
| High boilers | 0.05 |

In all cases, the aqueous base solution used was 32% sodium hydroxide solution, more specifically in a slightly substoichiometric amount in relation to phenolic hydroxyl groups.

Example 1 (Comparative Example)

ASPEN Simulation

Figure 2:
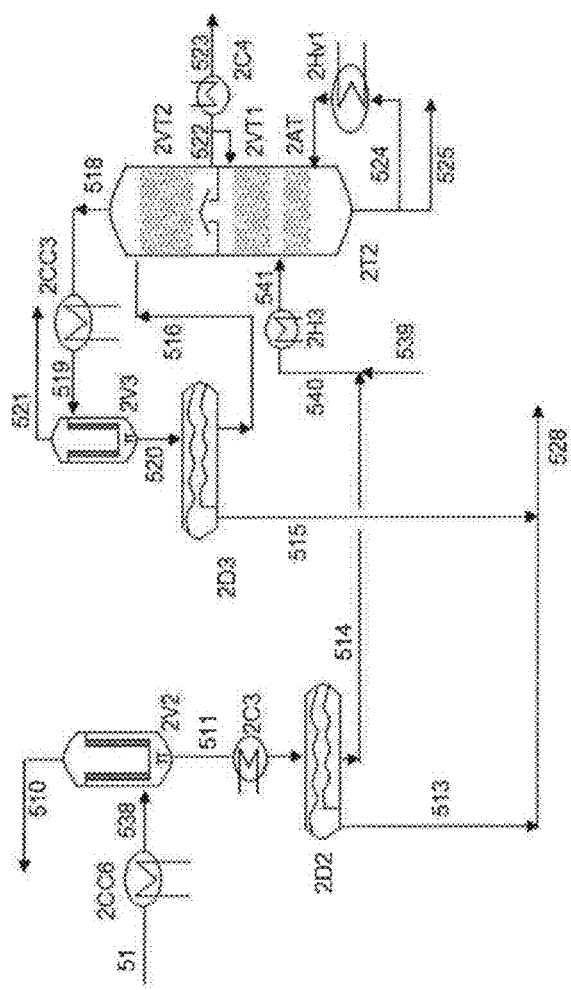
FIG. 2 is a side elevation view of a gas phase process for purification of aniline (according to comparative Example 1).

FIG. 2 shows the process employed in this example. The labels mean:

TABLE 3

Key for FIG. 2.

| Stream | Definition | Apparatus | Definition |
|---|---|---|---|
| 51 | gaseous crude reaction product (crude aniline) | 2CC6 | cycle gas cooler |
| 510 | gas stream from 2V2 | 2V2 | separator |
| 511 | bottoms output from 2V2 | 2C3 | cooler |
| 513 | aqueous phase from 2D2 | 2D2 | decanter |
| 514 | organic phase from 2D2 | 2H3 | preheater |
| 515 | aqueous phase from 2D3 | 2T2 | distillation column |
| 516 | organic phase from 2D3 | 2AT | stripping section |
| 518 | gas phase drawn off overhead from 2T2 | 2VT1 | lower rectifying section |
| 519 | top product from 2T2 after passing through 2CC3 | 2VT2 | upper rectifying section |
| 520 | bottoms output from 2V3 | 2Hv1 | evaporator |
| 521 | gas stream from 2V3 | 2C4 | cooler |
| 522 | aniline stream from side draw of 2T2 | 2CC3 | condenser |
| 523 | aniline stream from side draw of 2T2 after passing through 2C4 | 2V3 | separator |
| 524 | circulation to evaporator 2Hv1 | 2D3 | decanter |
| 525 | discharged bottoms output from 2T2 | 2CC6 | condenser |
| 528 | combined wastewater streams | | |
| 538 | crude reaction product after passing through 2CC6 | | |
| 539 | aqueous base solution | | |
| 540 | combined streams 514 and 539 | | |
| 541 | 540 after passing through 2H3 | | |

The following conditions were used as the basis:
Temperature of the gas downstream of 2CC6 (stream 538): 60° C.
Number of theoretical plates in the upper rectifying section of 2T2: 10
Number of theoretical plates in the middle rectifying section of 2T2: 9
Number of theoretical plates in the lower stripping section of 2T2: 12

In this process regime, the crude aniline stream 51 is not fractionally condensed, but is instead very substantially condensed (more than 95% of the aniline) in one step in the condenser 2CC6. The process product thus obtained (511—the "total condensate" of this process) is passed into a separator 2V2 for recycling of the uncondensed fractions in the hydrogenation process (via stream 510). The entire condensed crude product is cooled further in 2C3 and then subjected to a phase separation in the decanter 2D2. Sodium hydroxide solution (539) is fed into the organic phase 514 thus obtained. The NaOH-containing process product 540 obtained after passage through a suitable mixing unit is, after passing through a preheater 2H3, passed into the distillation column 2T2 between 2AT and 2VT1 (stream 541). The liquid output from the upper rectifying section 2VT2 is withdrawn completely as a sidestream (stream 522) and partly recycled back into the column as reflux to the middle rectifying section 2VT1. The unrecycled fraction is cooled in 2C4 and withdrawn as pure aniline stream 523. The mass flow rate of the bottom product, stream 525, is adjusted such that no phenoxide salts precipitate out in the bottom of 2T2. The gas phase conducted out in 2T2, stream 518, is cooled to 40° C., i.e. condensed, in 2CC3 with addition of inert gas, and passed into an apparatus for separation of gases and liquids (2V3). The offgas (stream 521) is sent to incineration. The liquid phase of 2V3 is separated into an aniline-rich phase and a water phase in the decanter 2D3. The aniline-rich phase is conducted as reflux to the top of the column 2T2 (516).

The process water phases from 2D2 (stream 513) and 2D3 (stream 515) are combined (stream 528) and can be passed into a water stripper, for example, for purification of the process water stream and for recovery of the aniline present. The aniline-rich stream obtained can be recycled, for example, into the decanter 2D3 (not considered as part of this example, since the energy expenditure for the water processing is about the same in all cases).

The results are compiled in table 2:

TABLE 4

Compositions of the streams and energy input necessary in example 1

| | Stream[a] | | |
|---|---|---|---|
| | 510 | 523 | 525 |
| Total mass flow rate | 13758 kg/h | 14725 kg/h | 320 kg/h |
| Uncondensable gases | 64.8% | <1 ppm | <1 ppm |
| Low boilers | 1.6% | 127 ppm | <1 ppm |
| Water | 28.4% | 0.10% | <1 ppm |
| Aniline | 5.1% | 99.9% | 92.0% |
| Sum total of pheno and sodium phenoxide | 4 ppm | 14 ppm | 2.5% |
| High boilers | <1 ppm | <1 ppm | 5.5% |
| Temperature | 60° C. | 40° C. | 150° C. |
| Pressure | | 3.1 bar (abs) | |
| Heat energy input needed for 2T2 | 0.286 kWh/kg of aniline in the product | | |

[a]Contents stated in % and ppm are always parts by mass.

As can be seen, this procedure involves the re-evaporation of all the aniline, in order to remove it from the high boilers. It is also necessary to accept significant aniline losses via stream 525, in order to avoid the precipitation of phenoxide salts in 2Hv1. The total energy input required for 2T2 is very high at 0.286 kWh/kg of aniline in the product.

Example 2 (Inventive)

ASPEN Simulation

This simulation was conducted on the basis of the process variant elucidated in FIG. 1 and already elucidated above. 5% of the liquid condensed in 1C2 is passed as stream 15 into the scrubber 1W1. The following conditions were used as the basis:
Temperature of stream 10 downstream of 1C1: 120° C.
Temperature of the gas downstream of 1C2 (stream 17): 85° C.
Pressure of the gas downstream of 1C2 (stream 17): 3.1 bar (abs)
Number of theoretical plates in 1W1: 6
Number of theoretical plates of 1D1: 10
Number of theoretical plates of 1D2: 10
Temperature downstream of 1C3: 60° C.

The results are compiled in table 5.

TABLE 5

Compositions of the streams and energy input necessary in example 2.

| | Stream[a] | | |
|---|---|---|---|
| | 40 (cycle gas) | 30 (pure aniline) | 60 (high boilers) |
| Total mass flow rate | 13857 kg/h | 15113 kg/h | 40 kg/h |
| Uncondensable gases | 64.4% | <1 ppm | <1 ppm |
| Low boilers | 1.7% | 338 ppm | <1 ppm |
| Water | 28.7% | 1.0% | <1 ppm |

TABLE 5-continued

Compositions of the streams and energy input necessary in example 2.

| | Stream[a] | | |
|---|---|---|---|
| | 40 (cycle gas) | 30 (pure aniline) | 60 (high boilers) |
| Aniline | 5.2% | 99.0% | 56.0% |
| Sum total of phenol and sodium phenoxide | 2 ppm | 23 ppm | 0.3% |
| High boilers | <1 ppm | 1 ppm | 43.7% |
| Temperature | 60° C. | 101° C. | 160° C. |
| Pressure | | 3.1 bar (abs) | |
| Heat energy input needed for 1D1 | 0.022 kWh/kg of aniline in the product | | |
| Heat energy input needed for 1D2 | 0.048 kWh/kg of aniline in the product | | |

[a]Contents stated in % and ppm are always parts by mass.

As can be seen, the use of the process according to the invention leads to a distinct reduction both in the energy consumption and in the aniline losses via stream 225. The total heat energy consumption in 1D1 and 1D2 is now only 0.070 kWh/kg compared to 0.286 kWh/kg of aniline in the product in the comparative example. The product quality differs only in that traces of phenoxide salts can occur in the product, but still in an acceptable amount. The product additionally contains more water than that of comparative example 1. However, if the product is subsequently used in a process comprising condensation reaction (for example the preparation of di- and polyamines of the diphenylmethane series), the higher water content is generally not disadvantageous. If desired, the water content can also be reduced to a lower level by a higher evaporation rate in 1C9. This, incidentally, is also a further advantage of the process according to the invention: if required, it is possible, in contrast to the procedure claimed in PCT/EP2011/068122 (see comparative examples 3 and 4), without further apparatus complexity, to obtain a virtually anhydrous product. In order to reduce the water content, for example, from 1% example 2 to 0.1% (comparable to comparative examples 1 and 3), only an additional 0.037 kWh/kg of aniline of heat energy is required in 1C9.

Example 3 (Comparative Example)

ASPEN Simulation

This example corresponds to the process according to PCT/EP2011/068122. This simulation is based on example 3 of the document, although, for reasons of compatibility, there is no consideration of the wastewater stripper and hence also of the incorporation of the aniline-containing stream recovered from the wastewater stream 327.

TABLE 6

Figure 3:
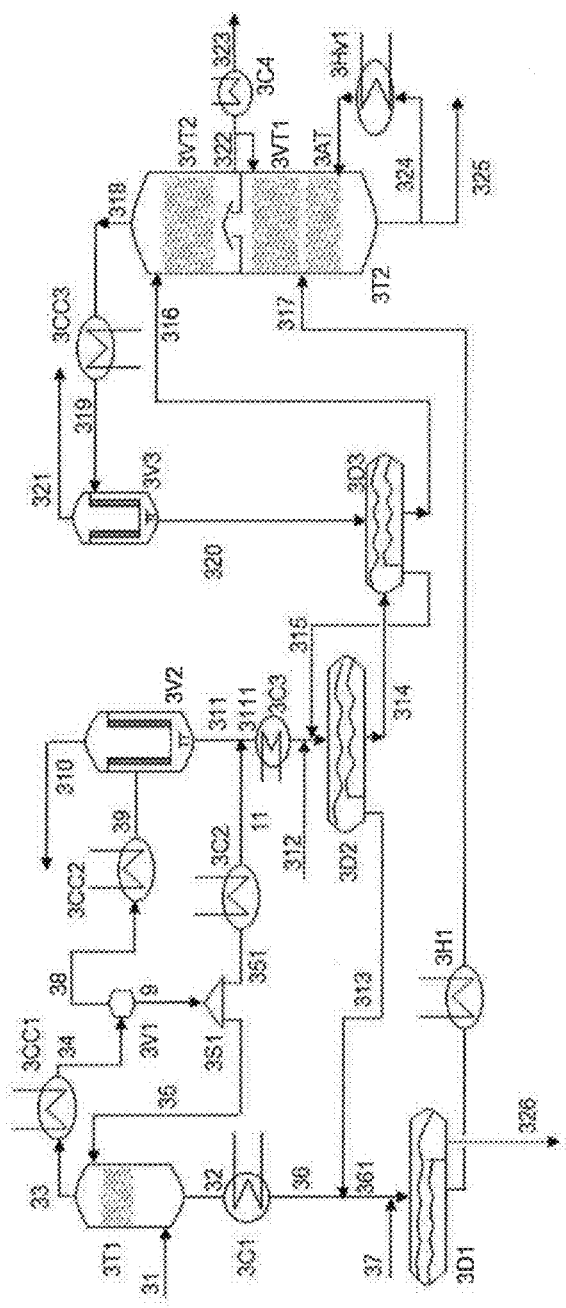
FIG. 3 is a side elevation view of a gas phase process for purification of aniline (according to comparative Example 3).

Key for FIG. 3.

| Stream | Definition | Apparatus | Definition |
|---|---|---|---|
| 31 | gaseous crude reaction product (crude aniline) | 3T1 | scrubber |
| 32 | liquid process product discharged from 3T1 | 3CC1 | condenser |
| 33 | gas stream from 3T1 | 3V1 | separator |
| 34 | 33 after passing through 3CC1 | 3S1 | splitter |
| 35 | product stream recycled into the top of 3T1 | 3C2 | cooler |

TABLE 6-continued

Key for FIG. 3.

| Stream | Definition | Apparatus | Definition |
|---|---|---|---|
| 351 | product stream branched off into 3S1, which is not recycled into 3T1 | 3CC2 | condenser |
| 36 | 32 after passing through 3C1 | 3V2 | separator |
| 361 | 36 after mixing with 313 | 3C3 | cooler |
| 37 | aqueous base solution | 3D2 | decanter |
| 38 | top product from 3V1 | 3C1 | cooler |
| 39 | 38 after passing through 3CC2 | 3D1 | decanter |
| 310 | gas stream from 3V2 | 3H1 | preheater |
| 311 | liquid process product discharged from 3V2 | 3D3 | decanter |
| 3111 | 311 after mixing with the stream from 3C2 | 3T2 | distillation column |
| 312 | aqueous base solution | 3AT | stripping section |
| 313 | aqueous phase from 3D2 | 3VT1 | lower rectifying section |
| 314 | organic phase from 3D2 | 3VT2 | upper rectifying section |
| 315 | aqueous phase from 3D3 | 3Hv1 | evaporator |
| 316 | organic phase from 3D3 | 3C4 | cooler |
| 317 | organic phase from 3D1 | 3CC3 | condenser |
| 318 | gas phase drawn off overhead from 3T2 | 3V3 | separator |
| 319 | 318 after passing through 3CC3 | | |
| 320 | liquid condensate stream drawn off from the bottom of 3V3 | | |
| 321 | gas stream from 3V3 | | |
| 322 | aniline stream from side draw of 3T2 | | |
| 323 | aniline stream from side draw of 3T2 after passing through 3C4 | | |
| 324 | circulation to evaporator 3Hv1 | | |
| 325 | discharged bottoms output from 3T2 | | |
| 326 | aqueous phase from 3D1 | | |
| 9 | liquid stream from 3V1 | | |
| 11 | 351 after passing through 3C2 | | |

The following conditions were used as the basis:
Temperature of the gas downstream of 3CC1 (stream 34): 85° C.
Pressure of the gas downstream of 3CC1 (stream 34): 3.1 bar (abs)
Number of theoretical plates in 3T1: 6
Number of theoretical plates of 3AT: 12
Number of theoretical plates of 3VT1: 9
Number of theoretical plates of 3VT2: 10
Temperature downstream of 3CC2: 60° C.
The results are compiled in table 7.

TABLE 7

Compositions of the streams and energy input necessary in example 3.

| | Stream[a] | | |
|---|---|---|---|
| | 310 (cycle gas) | 323 (pure aniline) | 325 (high boilers) |
|---|---|---|---|
| Total mass flow rate | 13857 kg/h | 15076 kg/h | 40 kg/h |
| Uncondensable gases | 64.4% | <1 ppm | <1 ppm |
| Low boilers | 1.7% | 352 ppm | <1 ppm |
| Water | 28.7% | 0.7% | <1 ppm |
| Aniline | 5.2% | 99.2% | 56.1% |
| Sum total of phenol and sodium phenoxide | 2 ppm | 19 ppm | 0.1% |
| High boilers | <1 ppm | 1 ppm | 43.7% |
| Temperature | 60° C. | 40° C. | 161° C. |
| Pressure | 3.1 bar (abs) | | |
| Heat energy input needed for 3Hv1 | 0.096 kWh/kg of aniline in the product | | |

[a]Contents stated in % and ppm are always parts by mass.

The heat energy requirement in 3Hv1, at 0.096 kWh/kg of aniline in the product, is about 40% higher than in inventive example 2. In addition, for the process according to example 3, the heat energy input has to be introduced at a high temperature level or with high-pressure steam, whereas, in inventive example 2, more than 50% of the total heat energy can be introduced (in apparatus 3C9) at a lower temperature level or with the aid of lower-value steam at a lower pressure level. In addition, the apparatus complexity in example 3 is significantly greater, since the basic scrubbing has to be effected separately for two streams.

Example 4 (Comparative Example)

ASPEN Simulation

This example corresponds to the process according to PCT/EP2011/068122. The calculation of the energy requirement included a product drying operation in a stripping column (4T4) to a residual water content of 1% by mass.

TABLE 8

Figure 4:
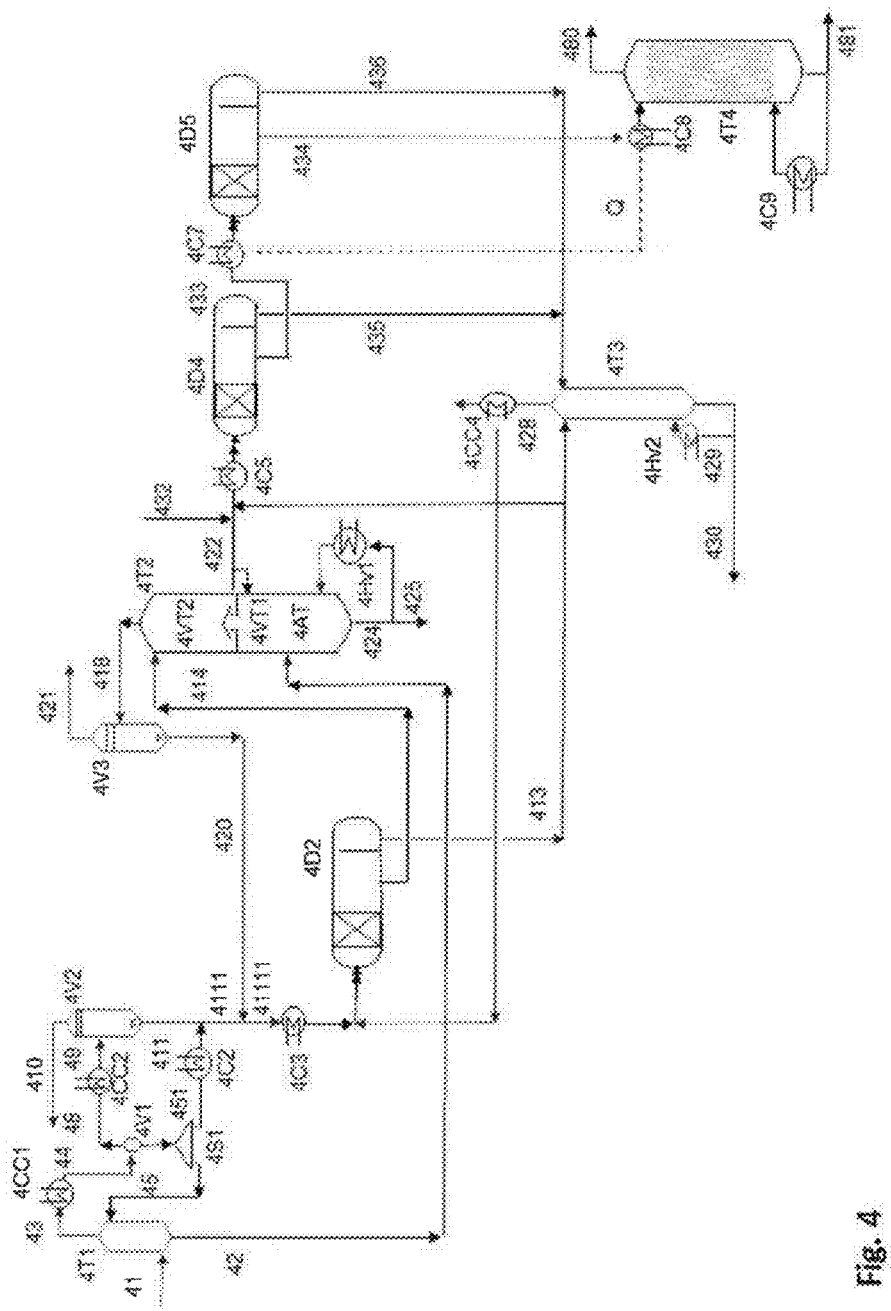
FIG. 4 is a side elevation view of a gas phase process for purification of aniline (according to comparative Example 4).

Key for FIG. 4.

| Stream | Definition | Apparatus | Definition |
|---|---|---|---|
| 41 | gaseous crude reaction product (crude aniline) | 4T1 | scrubber |
| 42 | liquid process product discharged from 4T1 | 4CC1 | condenser |
| 43 | gas stream from 4T1 | 4V1 | separator |
| 44 | 43 after passing through 4CC1 | 4S1 | splitter |
| 45 | product stream recycled into the top of 4T1 | 4C2 | cooler |
| 451 | product stream branched off into 4S1, which is not recycled into 4T1 | 4CC2 | condenser |
| 48 | gas stream from 4V1 | 4V2 | separator |
| 49 | 48 after passing through 4CC2 | 4C3 | cooler |
| 410 | gas stream from 4V2 | 4D2 | decanter |
| 411 | liquid process product discharged from 4V2 | 4T2 | distillation column |

TABLE 8-continued

Key for FIG. 4.

| Stream | Definition | Apparatus | Definition |
|---|---|---|---|
| 4111 | 411 after mixing with the stream from 4C2 | 4AT | stripping section |
| 41111 | 4111 after mixing with 420 | 4VT1 | lower rectifying section |
| 413 | aqueous phase from 4D2 | 4VT2 | upper rectifying section |
| 414 | organic phase from 4D2 | 4Hv1 | evaporator |
| 418 | gas phase drawn off overhead from 4T2 | 4V3 | separator |
| 420 | liquid condensate stream drawn off from the bottom of 4V3 | 4C5 | cooler |
| 421 | gas stream from 4V3 | 4D4 | decanter |
| 422 | aniline stream from side draw of 4T2 | 4D5 | decanter |
| 424 | circulation stream to evaporator 4Hv1 | 4CC4 | condenser |
| 425 | discharged bottoms output from 4T2 | 4T3 | water stripper |
| 428 | top product from 4T3 (aniline/water azeotrope) | 4Hv2 | evaporator |
| 429 | circulation stream to evaporator 4Hv2 | 4C7 | cooler |
| 430 | discharged bottoms output from 4T3 | 4C8 | heat exchanger |
| 432 | aqueous base solution | 4T4 | stripping column for drying of 434 |
| 433 | organic phase from 4D4 | 4C9 | evaporator |
| 434 | organic phase from 4D5 (= water-containing purified aniline) | | |
| 435 | aqueous phase from 4D4 | | |
| 436 | aqueous phase from 4D5 | | |
| 480 | gas stream from 4T4 | | |
| 481 | discharged bottoms output from 4T4 (dried aniline stream) | | |
| $\dot{Q}$ | heat integration between 4C7 and 4C8 | | |

The following conditions were used as the basis:
Temperature of the gas downstream of 4CC1 (stream 44): 85° C.
Pressure of the gas downstream of 4CC1 (stream 44): 3.1 bar (abs)
Number of theoretical plates in 4T1: 6
Number of theoretical plates of 4AT: 12
Number of theoretical plates of 4VT1: 9
Number of theoretical plates of 4VT2: 10
Number of theoretical plates of 4T3: 30
Number of theoretical plates of 4T4: 10
Temperature downstream of 4CC2: 60° C.

The results are compiled in table 9.

TABLE 9

Compositions of the streams and energy input necessary in example 4.

| | Stream[a] | | |
|---|---|---|---|
| | 410 (cycle gas) | 481 (pure aniline) | 425 (high boilers) |
| Total mass flow rate | 13857 kg/h | 15151 kg/h | 40 kg/h |
| Uncondensable gases | 64.4% | <1 ppm | <1 ppm |
| Low boilers | 1.7% | 329 ppm | <1 ppm |
| Water | 28.7% | 1.0% | <1 ppm |
| Aniline | 5.2% | 99.0% | 53.8% |
| Sum total of phenol and sodium phenoxide | 2 ppm | 23 ppm | 2.5% |
| High boilers | <1 ppm | 1 ppm | 43.7% |
| Temperature | 60° C. | 119° C. | 161° C. |
| Pressure | 3.1 bar (abs) | | |
| Heat energy input needed for 4Hv1 | 0.070 kWh/kg of aniline in the product | | |
| Heat energy input needed for 4C9 | 0.044 kWh/kg of aniline in the product | | |

[a]Contents stated in % and ppm are always parts by mass.

According to example 4, as in inventive example 2, it is necessary to subject only one stream to a basic scrubbing operation. However, the heat energy requirement, at 0.114 kWh/kg of aniline in the product, is about 60% higher than in inventive example 2.

What is claimed is:
1. A process for preparing aniline, comprising the following steps:
(i) hydrogenating nitrobenzene in the gas phase in the presence of a catalyst,
(ii) fractionally condensing the gaseous crude product obtained in (i) in n condensation stages, wherein:
n represents a natural number from 2 to 8, with gradually falling condensation temperature, thereby forming a liquid partial condensate $PK^i$ ($PK^1$, $PK^2$, ... $PK^{n-1}$) in each of the first to $(n-1)^{th}$ condensation stages and a liquid total condensate (TK) in the $n^{th}$ condensation stage,
(iii) (a) when n=2, distilling the one liquid partial condensate $PK^1$ obtained in (ii), and

(b) when n≥3, distilling some of the liquid partial condensates $PK^i$ obtained in (ii),
to obtain a distillate PKD,
(iv) combining
  (a) if present, at least some of the partial condensates $PK^i$ formed in (ii) and not distilled in (iii),
  (b) the distillate PKD obtained in (iii),
  and
  (c) at least the organic fraction of the total condensate TK,
  and extracting the product mixture thus obtained with aqueous base solution and separating the mixture thus obtained into an aqueous phase and an organic, aniline-comprising phase.

2. The process as claimed in claim 1, in which the total condensate, prior to performance of step (iv), is separated into an organic phase (TKO) and an aqueous phase (TKW), and in step (iv), (c) only the organic phase TKO is combined with (a) if present, at least some of the partial condensates $PK^i$ formed in (ii) and not distilled in (iii), and (b) the distillate PKD obtained in (iii).

3. The process as claimed in claim 2, in which the organic, aniline-comprising phase obtained in (iv) is
  (v) washed with a stream comprising at least 85% by mass of water, based on the total mass of this stream.

4. The process as claimed in claim 3, in which the stream comprising at least 85% by mass of water is the aqueous phase TKW separated from the nth condensate or a portion thereof.

5. The process as claimed in claim 1, in which step (ii) comprises exactly three condensation stages.

6. The process as claimed in claim 1, in which the first condensation stage is operated at a temperature $T^1$ of 100° C. to 200° C., and the nth condensation stage at a temperature $T^n$ of 15° C. to 90° C., and the temperature of every further condensation stage, if present, is 1 K to 100 K below the preceding condensation stage.

7. The process as claimed in claim 1, in which the organic, aniline-comprising phase obtained in (iv) is
  (v) washed with a stream comprising at least 85% by mass of water, based on the total mass of this stream.

8. The process as claimed in claim 7, in which the stream comprising at least 85% by mass of water has been obtained by condensation of water-containing vapors.

9. The process as claimed in claim 7, in which the washed organic, aniline-comprising phase obtained in (v) is stripped.

10. The process as claimed in claim 1, in which the organic, aniline-comprising phase obtained in (iv) is stripped.

11. The process as claimed in claim 1, in which the aqueous base solution used in step (iv) is a solution of an alkali metal hydroxide, alkaline earth metal hydroxide, or a mixture of alkali metal hydroxide and alkaline earth metal hydroxide in water.

12. The process as claimed in claim 1, in which all the aqueous streams obtained are combined and the combined wastewater stream is subjected to stripping in order to recover aniline as an azeotrope with water.

* * * * *